US011987004B2

(12) United States Patent
Guillemot et al.

(10) Patent No.: US 11,987,004 B2
(45) Date of Patent: May 21, 2024

(54) ENCLOSED BIOPRINTING DEVICE

(71) Applicant: Poietis, Pessac (FR)

(72) Inventors: Fabien Guillemot, Preignac (FR); Bertrand Viellerobe, Merignac (FR)

(73) Assignee: Poietis, Pessac (FR)

( * ) Notice: Subject to any disclaimer, the term of this patent is extended or adjusted under 35 U.S.C. 154(b) by 288 days.

(21) Appl. No.: 17/287,873

(22) PCT Filed: Oct. 24, 2019

(86) PCT No.: PCT/FR2019/052541
§ 371 (c)(1),
(2) Date: Apr. 22, 2021

(87) PCT Pub. No.: WO2020/084262
PCT Pub. Date: Apr. 30, 2020

(65) Prior Publication Data
US 2021/0394444 A1 Dec. 23, 2021

(30) Foreign Application Priority Data
Oct. 25, 2018 (FR) ..................................... 18 59889

(51) Int. Cl.
*B29C 64/379* (2017.01)
*B29C 64/268* (2017.01)
(Continued)

(52) U.S. Cl.
CPC .......... *B29C 64/379* (2017.08); *B29C 64/268* (2017.08); *B29C 64/321* (2017.08);
(Continued)

(58) Field of Classification Search
CPC ... B29C 64/379; B29C 64/268; B29C 64/321; B29C 64/393; B29C 64/364; B33Y 40/00; B33Y 70/00; C12M 21/08
See application file for complete search history.

(56) References Cited

U.S. PATENT DOCUMENTS

2010/0206224 A1* 8/2010 Thurner ................ B29C 64/106
118/620
2016/0068793 A1* 3/2016 Maggiore ............. B29C 64/188
901/22
(Continued)

FOREIGN PATENT DOCUMENTS

WO WO-2016097620 A1 * 6/2016 ........... B29C 64/112

OTHER PUBLICATIONS

International Search Report for International Application No. PCT/FR2019/052541 dated Feb. 4, 2020, 3 pages.
(Continued)

Primary Examiner — Michael M. Robinson
(74) Attorney, Agent, or Firm — TraskBritt

(57) ABSTRACT

A bioprinting system comprises: a) a printing module containing at least one printhead for printing transferable objects of biological interest and at least one target, b) a feed source for the printhead for printing objects of biological interest, c) an activation means for the transfer of the objects of biological interest to the target, d) a means for relative displacement of the printhead with respect to the target, e) a sterilizable sealed enclosure, characterized in that —the printing module is placed the sterilizable sealed enclosure —the activation means is located outside of the sterilizable sealed enclosure, —and the sterilizable sealed enclosure has a leaktight interaction zone with the activation means.

12 Claims, 9 Drawing Sheets

(51) Int. Cl.
  *B29C 64/321* (2017.01)
  *B29C 64/393* (2017.01)
  *B33Y 40/00* (2020.01)
  *B33Y 70/00* (2020.01)

(52) U.S. Cl.
  CPC ............ *B29C 64/393* (2017.08); *B33Y 40/00* (2014.12); *B33Y 70/00* (2014.12)

(56) References Cited

U.S. PATENT DOCUMENTS

2016/0297152 A1* 10/2016 Maggiore .............. B33Y 10/00
2017/0320263 A1* 11/2017 Guillemot ............ B41J 2/14104
2017/0335271 A1* 11/2017 Maggiore .............. B29C 48/02
2018/0290386 A1   10/2018 Deciccio

OTHER PUBLICATIONS

International Written Opinion for International Application No. PCT/FR2019/052541 dated Feb. 4, 2020, 6 pages.

* cited by examiner

20

US 11,987,004 B2

ENCLOSED BIOPRINTING DEVICE

CROSS-REFERENCE TO RELATED APPLICATIONS

This application is a national phase entry under 35 U.S.C. § 371 of International Patent Application PCT/FR2019/052541, filed Oct. 24, 2019, designating the United States of America and published as International Patent Publication WO 2020/084262 A1 on Apr. 30, 2020, which claims the benefit under Article 8 of the Patent Cooperation Treaty to French Patent Application Serial No. 1859889, filed Oct. 25, 2018.

TECHNICAL FIELD

The present disclosure relates to the field of regenerative medicine making it possible to artificially produce organs and biological tissues, referred to as "tissue engineering." The need for tissue and organ transplants has increased dramatically around the world over the past decade. The main reasons are the increase in life expectancy, the incidence of vital organ dysfunction and degenerative diseases, and the need to alleviate the consequences of tumor removal. Due to this organ shortage, in the European Union alone, more than 63,000 patients are waiting for an organ transplant (kidney, liver, heart, cornea, etc.) and 6 new patients are added to the waiting lists every hour. In contrast, only around 33,000 donors were identified in 2016. While some countries are taking steps to increase the number of organ donations, many patients awaiting transplants will not receive them in time. Clinicians therefore need tissue and organ substitutes that are well characterized and safe, patient-specific and potentially "off the shelf."

BACKGROUND

In this respect, scientists and industrialists in the field of tissue engineering apply the principles of biology and engineering to develop functional substitutes, which restore, maintain or improve tissue function.

From a regulatory point of view, tissue engineered products belong to the category of Advanced Therapy Medicinal Products (ATMP). They are distinct from conventional pharmaceuticals and therefore present unique challenges. They require quality assurance and complex logistics, and must be transplanted into patients by qualified surgeons, while meeting important regulatory requirements such as the regulation of Advanced Therapy Medicinal Products (ATMP) as well as Good Laboratory Practices (GLP) and Good Manufacturing Practices (GMP).

Tissue engineering approaches traditionally rely on the use of biocompatible materials, shaped to form a 3D scaffold on which living cells are seeded before their maturation in a bioreactor. Then, as the cells multiply, they populate the scaffold and synthesize an extracellular matrix to create 3D tissue.

Despite substantial investments made to meet clinical and commercial expectations, and while the scientific achievements at the preclinical research stage have been impressive, these traditional tissue engineering approaches struggle to both deliver clinical results and become cost-effective. Indeed, a very small number of tissue engineered products have obtained their marketing authorization to date, and even in these cases, the therapeutic benefit has not met expectations and the marketing was not profitable. This is illustrated by the fact that three of these ATMPs were withdrawn from the market, despite sufficient safety and efficacy: PROVENGE (2015), CHONDROCELECT® (2016) and MACI® (suspended).

In order to meet clinical and commercial expectations, the manufacture of tissue engineered products is therefore subject to several challenges that must be resolved. These concern:

industrialization and automation of manufacturing methods in order to increase their robustness, knowing that the manufacture of ATMPs is still mainly manual, unsupervised and includes multiple open stages, compliance with regulatory requirements, improving profitability and cost-effectiveness, for example, by reducing the high costs of supplying consumables, installing and owning infrastructure (e.g., clean rooms) and equipment, and specialized labor necessary for carrying out the various preparation, manufacture and quality control operations of small individual batches in low volumes, the ability to replicate the complexity of native human tissues (i.e., the spatiotemporal distribution of cells and biochemical, mechanical and physical stimuli that control the cellular microenvironment and govern cell behavior and tissue function), the need to promote rapid vascularization after implantation in order to maintain cell viability during tissue growth, and in some cases, the ability to customize tissue engineered products to provide patient-specific treatments (e.g., by integrating autologous cells and/or patient anatomy data).

To confront the limits of traditional tissue engineering approaches, different bioprinting approaches have been proposed. According to the published works, these printing methods are called biological printing, micro-printing of biological elements or bioprinting. These use the principles of 3D printing, and proceed by the layer-by-layer assembly of the constituents of biological tissues (such as cells and the extracellular matrix) according to organizations predefined by digital design. Despite the analogies in principle, it should be noted that bioprinting differs from the manufacture of prostheses by 3D printing in the nature of the deposited material (living and not inert) as well as in the technologies used.

The main use of bioprinting relates to the preparation of synthetic living tissues for experimental research, by replacing tissues taken from living beings, in order to avoid regulatory and ethical problems. In the longer term, bioprinting will allow the production of organs for transplantation without the rejection risks, for example, of the epidermis, bone tissue, parts of the kidney, liver as well as on other vital organs, heart valves or hollow structures such as vascular structures.

The global 3D bioprinting market was estimated at 450 million euros in 2014 and is expected to increase significantly over the next decade at an annual growth rate of around 16.7%, reaching 8.2 billion euros by 2025 1. According to analysts, the medical segment of the bioprinting market is expected to dominate in 2022 with more than 30.0% owing to the introduction of bioprinters compatible with the manufacture of ATMP.

Patent application US2017335271 is known in the state of the art, describing a portable device comprising a first element for dispensing a structural material and a second disposable element for dispensing a biological material.

The delivery system also comprises a sterilizable enclosure and at least one robotic arm assembly and a delivery device within the sterilizable chamber. The robotic arm is configured to move the delivery device comprising a first delivery member and a second delivery member, the first delivery member being removably connectable to the second delivery member.

FIGS. 10 and 11 of this patent mainly relate to the handling of well plates, with a printhead and the activation module both housed in the sterile enclosure, unlike the present disclosure.

This solution does not allow the manufacture by additive printing of biological tissues under optimal sterility conditions.

American patent application US2010206224 is also known, which relates to a device for depositing layers, comprising:
- a frame fitted with an enclosure and further bearing:
  - a table intended to support an object to be manufactured,
  - a material dispenser intended to place the material on the table in order to form the object,
  - compaction means,
and a control member intended to control the deposit of material on the table.

Arranged inside the enclosure are at least the plate and the end of the nozzle, and arranged outside the enclosure are at least the means for moving the table and the dispenser and the control means.

This document does not relate to a system for bioprinting a biological tissue.

Patent application US2018290386 describes a method of the prior art with steps for creating pharmaceutical products by a 3D printer. A product is printed according to the instructions. At least one attribute of the product is measured and compared to the desired attributes of the desired end product. If there is a difference between the product attributes and the desired attributes, changes are made to the set of instructions and a new product is printed. When there is a match between product attributes and desired attributes, a safe and accurate medical product has been created.

It is not a solution for the manufacture of biological tissues.

Patent application US2017320263 describes a method for printing at least one biological ink, the method using at least one laser-type printhead to deposit at least one droplet of at least one biological ink on a depositing surface of a recipient substrate, characterized in that the printing method uses at least one nozzle printhead to deposit at least one droplet of at least one biological ink on a deposit surface of the same receiver substrate as the laser-type printhead. This is believed to be the closest state of the art, but requires a very restrictive clean room-type environment for the operators.

Patent application US2016297152 relates to a sterilizable container intended to receive one or more bioactive fluid(s) and/or one or more preparatory fluid(s) comprising:
- an area inside the container configured to receive at least one sterilizable 3D printer assembly;
- a sterilizable 3D printer assembly comprising:
  - at least one printing platform;
  - at least one printhead for dispensing a structural material on the printing platform(s) in order to form a three-dimensional structure thereon; and
  - a movement mechanism allowing relative displacement between the printhead(s) and the printing platform (s), the area being configured so that fluid can reach the printer assembly.

The solution presented by international application US2017320263 has the drawback of involving the treatment of a large volume of air necessary to contain the bioprinting equipment in an aseptic state, which implies high air flow rates in order to create an overpressure, with a high risk of turbulence in the bioprinting area, which is particularly prohibitive for the reproducibility of the prints whatever the bioprinting technique used.

In addition, such a flow rate requires a powerful fan, which is a source of vibrations and noise pollution, and a filter developed to allow the passage of a large air flow while retaining all the particles.

Furthermore, the presence of mechanical equipment in the sterile chamber leads to the production of microparticles, which are conveyed by the air flow into the bioprinting space, which goes against the intended objective. Thus, in the two examples cited in the prior art, it can be emphasized that the printing means are directly integrated into the sterilizable area. Now, these elements are among the main contributors to particulate pollution in confined spaces.

Finally, when changing the bioprinting sequence, the risk of pollution or cross-contamination between samples is high, because the different samples follow one another in the same chamber and are interchanged outside the sterilization phases.

BRIEF SUMMARY

In order to remedy these drawbacks, the present disclosure relates to a method and a unit for manufacturing a biological tissue by bioprinting using three distinct modules:
- A printing module integrating the printhead, imperatively placed inside the sterilizable enclosure;
- An activation module (a laser, a transducer, etc.) for transferring biological objects to a target via the printhead, imperatively placed outside the sterilizable enclosure; and
- A module for moving the printhead relative to the target, positioned either inside or outside the sterilizable enclosure.

The enclosure comprises an interaction zone with the activation module.

The present disclosure particularly relates to a method and a unit for the additive printing of biological tissues by unitary deposit on a target of elements comprising living cells, as well as other constituents making it possible to reconstitute living biological tissue.

In its most general sense, a bioprinting system according to claim 1, and optionally including technical features of a dependent claim, taken alone or in a technically feasible combination of other features described below.

The object of the present disclosure is to transfer, from a source to a target, objects of biological interest comprising living cells (for example, pluripotent stem cells or any other differentiated cells), sometimes of different types, as well as biologicals products such as collagen and more generally extracellular matrix materials.

The objects of biological interest can be brought together in a fluid to form a "bio-ink" containing biological particles such as, for example, living cells. These bio-inks are then prepared and packaged in sterile form, so that they can be used to print biological tissue when the time comes.

Within the meaning of the present patent, "bioprinting" designates the spatial structuring of living cells and other biological products, by a method carrying out a computer-assisted geometric structuring, in particular, a stack of layers formed by individualized deposits of objects of biological interest, to develop living tissues and organs for tissue engineering, for regenerative medicine, pharmacokinetics and more generally for research in biology. Bioprinting involves the simultaneous deposition of living cells and biomaterials layer by layer in order to make living tissues such as artificial structures of the skin, heart valves, cartilage, heart tissue, kidneys, liver as well as on other vital organs or hollow structures such as the bladder as well as vascular structures.

The present disclosure also relates to a cassette for a bioprinting system as referred to above, characterized in that it consists of a sterilizable sealed enclosure constituting the jacket of a printing module.

The present disclosure also relates to a bioprinting method for the manufacture of a structured biological material, from materials consisting at least in part of biological particles (cells and cellular derivatives), consisting in controlling the movement of at least one target via a robot in three dimensions facing at least one printhead placed in a sealed and sterile enclosure, the printhead being supplied and controlled from outside the enclosure in order to guarantee the safety of the produced tissue with regard to regulatory requirements in the clinical field.

BRIEF DESCRIPTION OF THE DRAWINGS

The present disclosure will be better understood on reading the detailed description of a non-limiting example of the present disclosure, which follows, with reference to the accompanying drawings, where.

DETAILED DESCRIPTION

Figure 1:
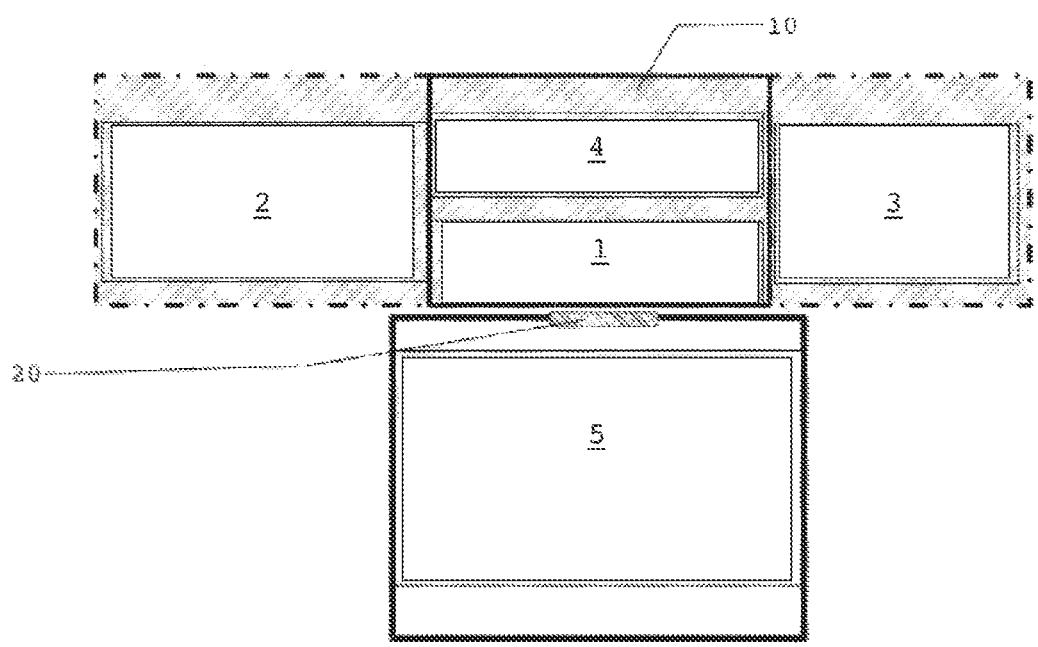
FIG. 1 shows a schematic view of a first variant of a bioprinter according to the present disclosure.

FIGS. 1 to 5 show views of variant embodiments of the hardware architecture of a bioprinter according to the present disclosure. It is made up of several essential members:

An additive printhead (1), the configuration of which depends on the technology used, comprising a bio-ink transfer area made up of objects of biological interest and a target (6).

One or more feed sources (2) for feeding the additive printhead (1) with bio-ink consisting of objects of biological interest.

A mechatronic assembly (3) ensuring the relative displacement of the transfer area with respect to the target (6).

Optionally, a maturation area (4).

A printing activation means (5), the configuration of which depends on the technology used.

The term "bioprinting head" refers to the part of the bioprinting system formed by the support receiving the bio-still or more generally the objects of biological interest to be transferred to the target, and presenting the exit area of the objects of biological interest toward the target, but not comprising the activation means, for example:

For laser bioprinting, the bioprinting head does not comprise the laser and optical components for pulsed laser bioprinting.

For inkjet or microvalve bioprinting, the bioprinting head does not comprise the electrical generation means, which enable the actuator (valve/piezo) to be activated.

For micro-extrusion bioprinting, the bioprinting head does not comprise syringe pumps.

In general, two parts can be distinguished in biological bioprinting equipment:

A part designated within the meaning of this patent by "printhead (1)," consisting of the terminal part of the equipment, receiving the bio-ink and/or the objects of biological interest to be transferred as well as the interfaces for the transfer activation members.

A part designated within the meaning of the present patent by "activation means (5)," which is physically separable from the printhead (1), and mechanically, electrically, acoustically or optically coupled with the bioprinting head, comprising all the means making it possible to control the physical transfer of an object of biological interest present in the bioprinting head to the target.

The present disclosure aims to optimize the sterile area, and to this end:

a) the printhead (1) must be placed in a sterilizable enclosure (10), b) the printing means (5) must be placed outside the sterilizable enclosure (10), c) a leaktight interaction zone (20) allows the activation of the printhead (1) by the printing means (5).

The other components of the bioprinter can be placed in the sterilizable enclosure (10) or outside this enclosure (10).

In particular, the feed source (2) can be associated with the printhead (1) in the sterilizable enclosure (10), which then forms a cassette, which can be introduced into a bio-printer, then withdrawn for the maturation of the printed tissue.

The mechatronic assembly (3) for moving the target (6) relative to the source can also be associated with the printhead (1) inside the sterilizable enclosure (10), with or without the feed source (2).

The maturation chamber (4) can also be associated with the printhead (1) inside the enclosure (10), with or without the feed source (2) and/or the mechatronic movement assembly (3).

Alternative Embodiments

The present disclosure can be implemented in different ways.

FIG. 1 shows a generic view where the sterilizable enclosure (10) contains:

As a requirement, the printhead (1), and optionally, a maturation area (4) in which is placed the target receiving the transferred objects of biological interest;

Optionally the feed source (2), for example, the bio-ink reservoir and the feed system, which, according to the present disclosure can also be arranged in a non-sterile area, with a connector for the sterile transfer of objects of biological interest into the sterilizable enclosure (10); and Optionally, the movement means (3) for moving the printhead (1), which, according to the present disclosure, can also be placed in a non-sterile area, with a sterile mechanical connector.

The activation means (5), for example, the laser and the associated optical components, is placed below this sterilizable enclosure (10), a transparent window (20) forming the interface allowing the passage of the light beams. The activation means (5) is not placed in a sterile area.

Figure 2:
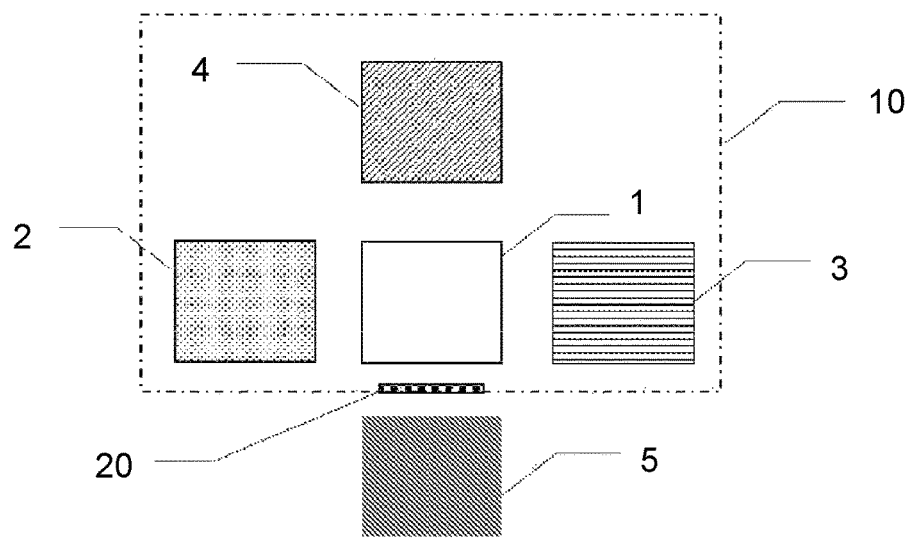
FIG. 2 shows a schematic view of a second variant of a bioprinter according to the present disclosure.

FIG. 2 shows a variant where all the constituents, with the exception of the activation means (5), are placed in the sterilizable enclosure (10).

Figure 3:
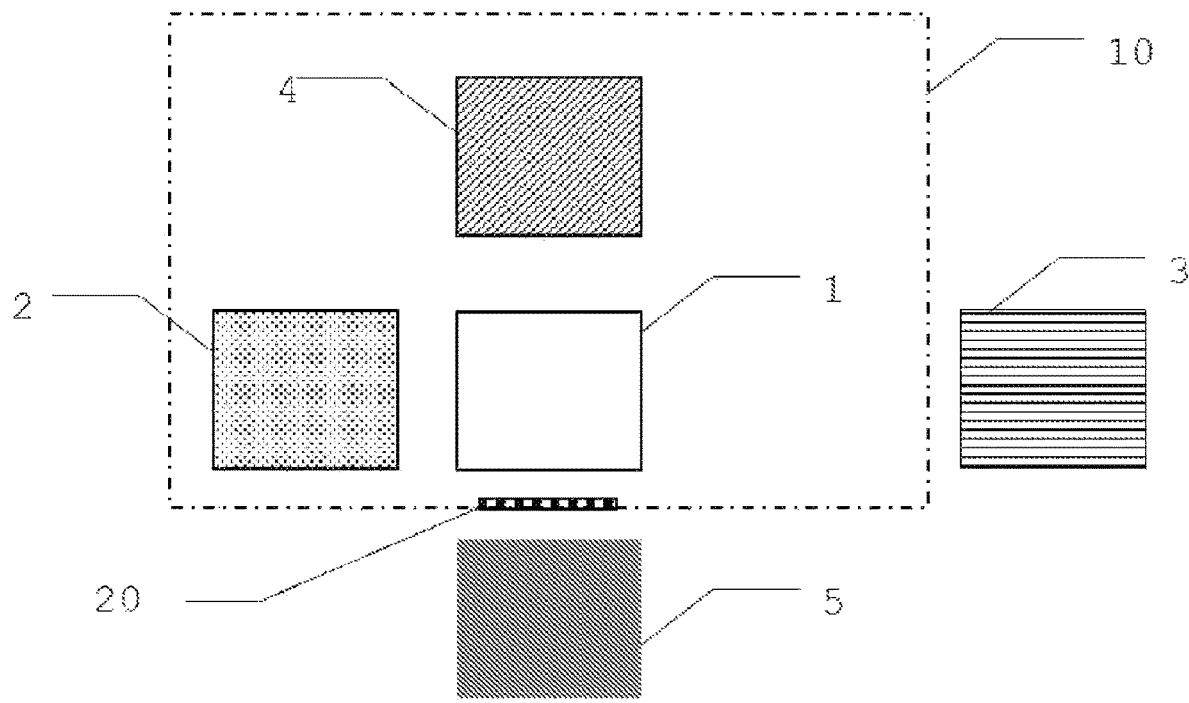
FIG. 3 shows a schematic view of a third variant of a bioprinter according to the present disclosure.

FIG. 3 shows a variant in which all the constituents, with the exception of the activation means (5) and of the movement means (3) for moving the printhead (1), are placed in the sterilizable enclosure (10). The coupling between the printhead (1) and the movement means (3) is achieved, for example, by a magnetic transmission or by a sterile articulation passing through the wall of the sterilizable enclosure (10).

Figure 4:
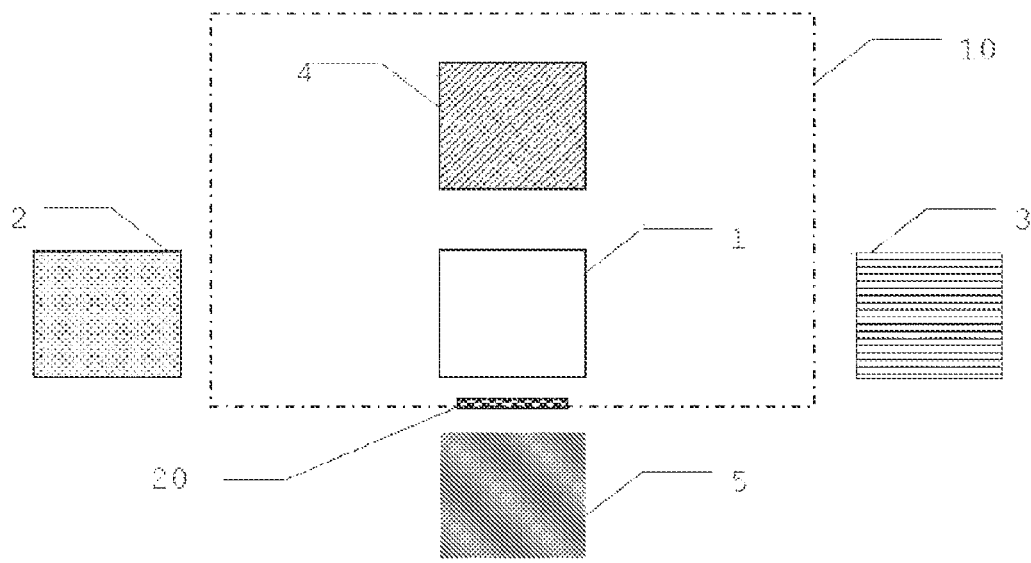
FIG. 4 shows a schematic view of a fourth variant of a bioprinter according to the present disclosure.

FIG. 4 shows a variant where only the printhead (1) and a maturation area (4) are placed in the sterilizable enclosure (10). All the other components, in particular, the activation means (5) and the movement means (3), as well as the feed source (2), are outside the sterilizable enclosure.

FIG. 4 shows a variant where only the printhead (1) and a maturation area (4) are placed in the sterilizable enclosure (10), along with the movement means (3). All the other constituents, in particular, the activation means (5) as well as the feed source (2), are outside the sterilizable enclosure.

Figure 5:
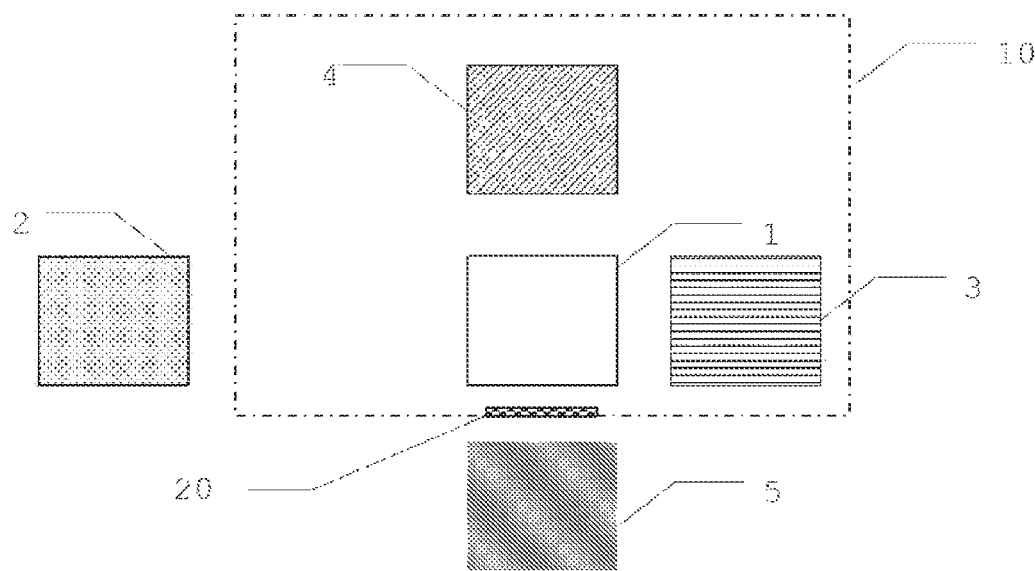
FIG. 5 shows a schematic view of a fifth variant of a bioprinter according to the present disclosure.
Figure 6:
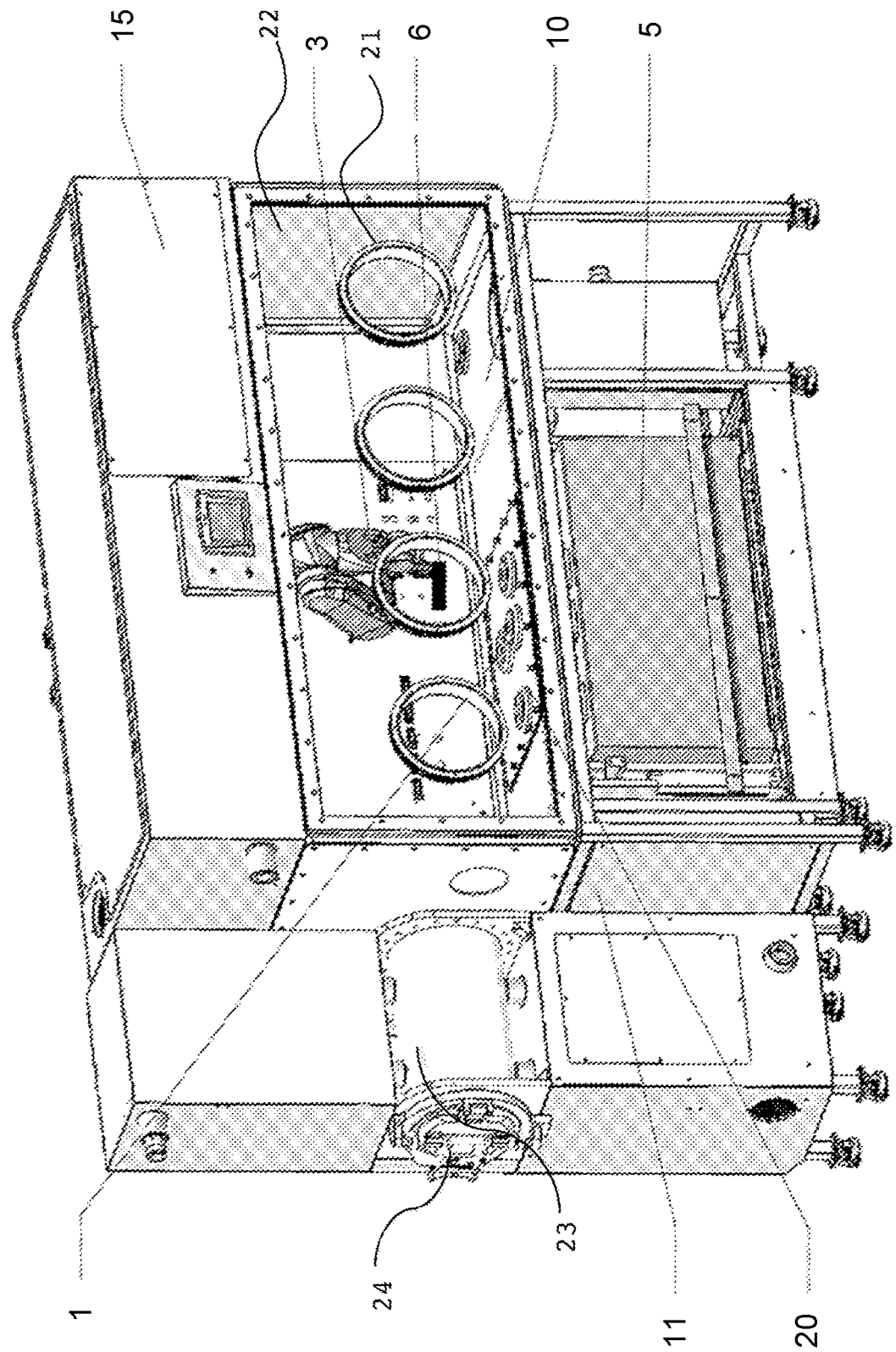
FIG. 6 shows a perspective front view of an embodiment of the present disclosure.
Figure 7:
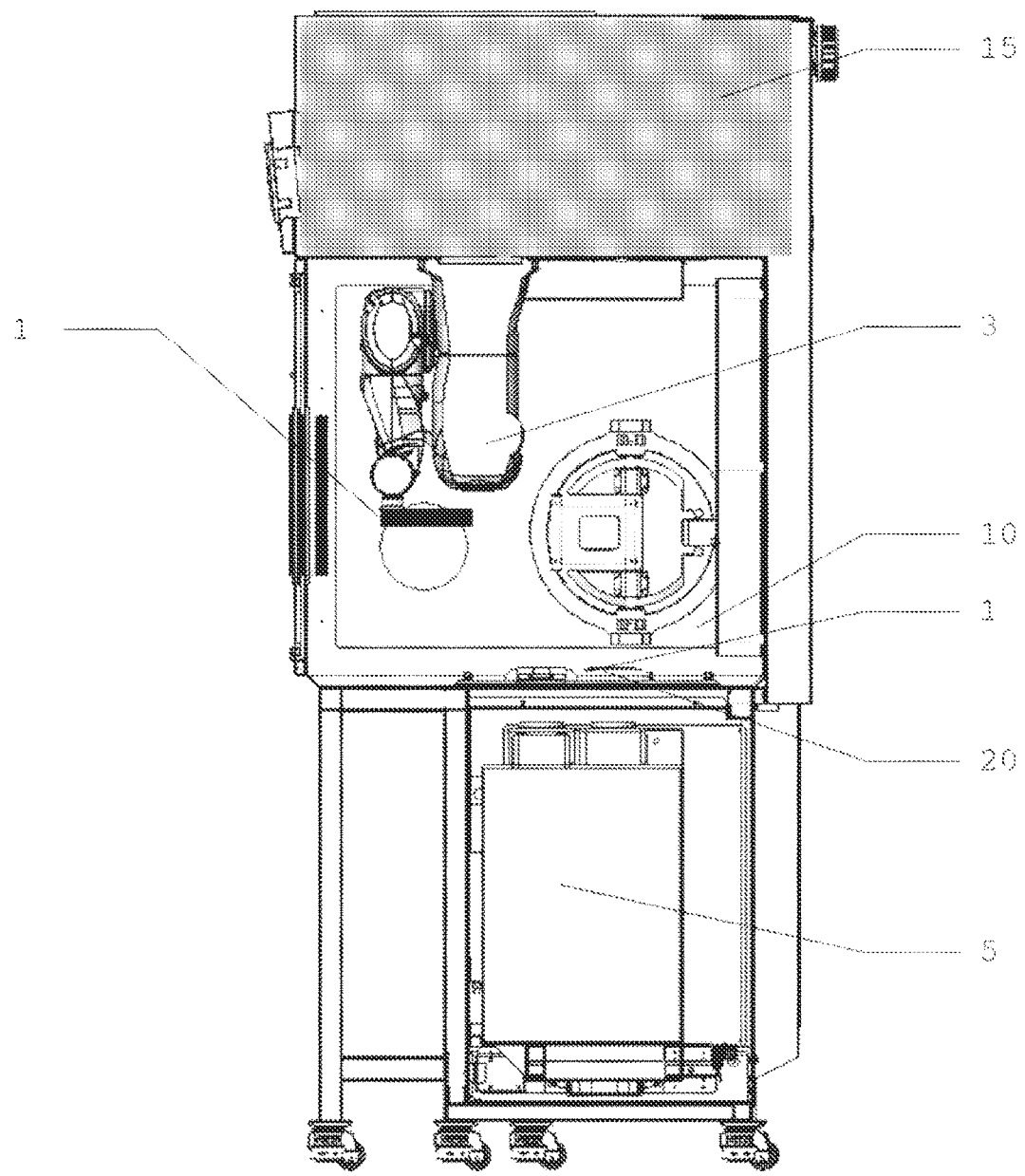
FIG. 7 shows a perspective side view of an embodiment of the present disclosure.
Figure 8:
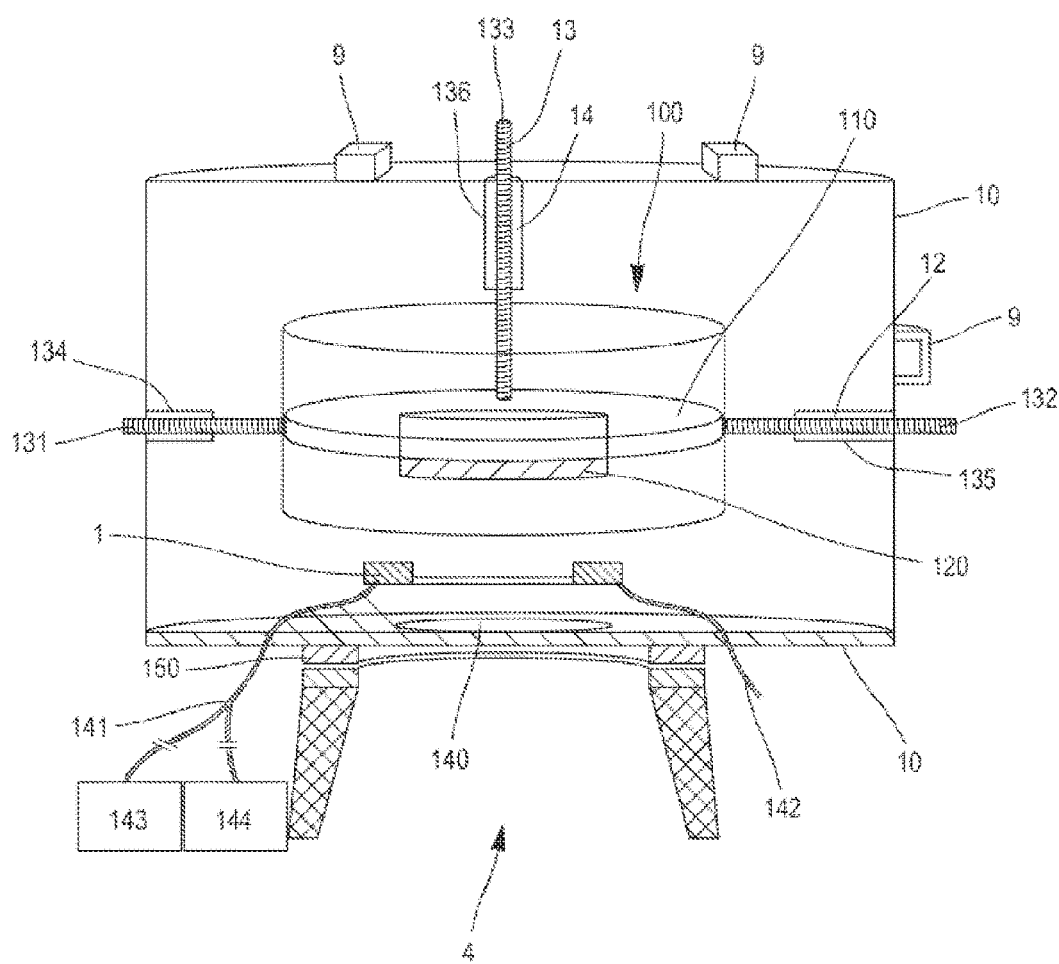
FIG. 8 shows a schematic view of an alternative embodiment in the form of a rigid cassette.
Figure 9:
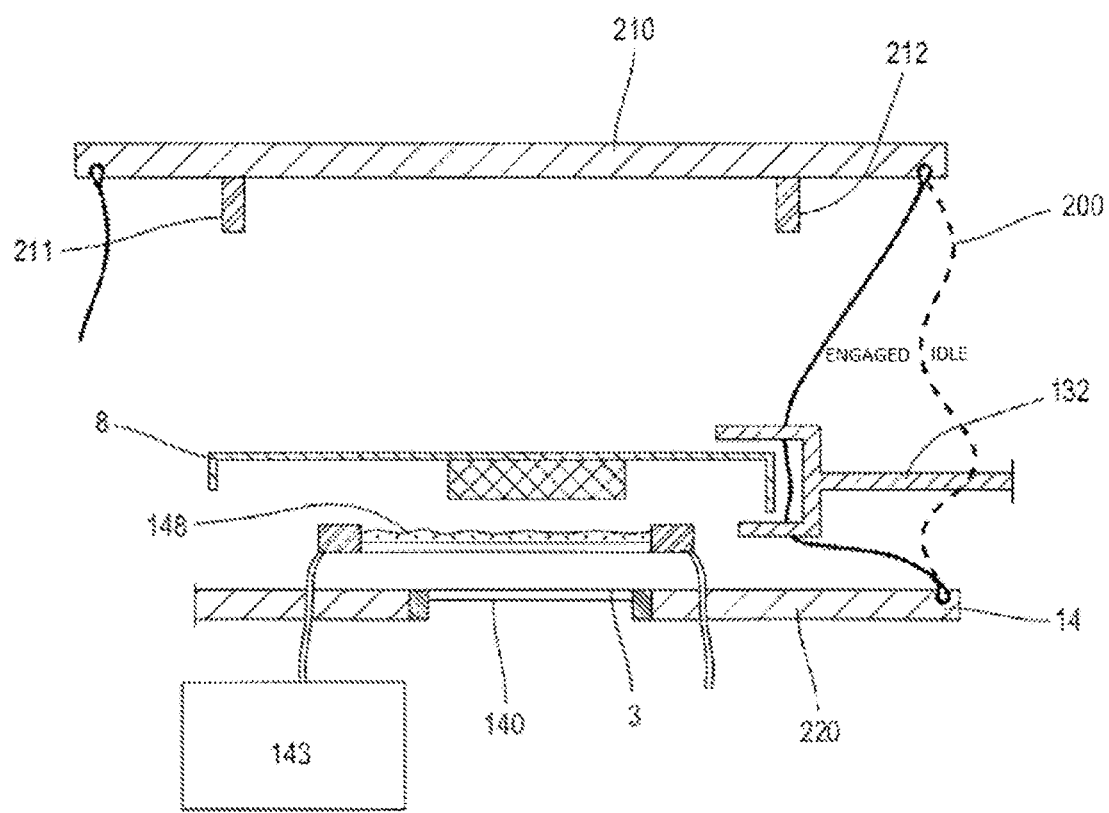
FIG. 9 shows a schematic view of an alternative embodiment in the form of a flexible cassette.

FIG. 5 shows a variant where the printhead (1), a maturation area (4) and the robotic arm (3) ensuring the relative displacement of the printhead (1) with respect to the target are placed in the sterilizable enclosure (10). Only the activation means (5) and the feed source (2) are outside the sterilizable enclosure.

Description of One Embodiment

The bioprinter consists of a base, the—not sterilizable—lower part (11) of which contains the activation means (5), for example, the optical head, the laser and the imaging systems for a laser printer.

This frame is topped by a sterilizable enclosure (10) consisting of a positive pressure chamber supplied by a blower (15) via a filter cartridge (16). A robotic arm (3) placed in this sterilizable enclosure (10) ensures the movement of a target (6) relative to a printhead (1). A leaktight window (20) allows the transmission of the laser beam and the imaging beams between the sterilizable enclosure (10) and the printing means (5) placed in the non-sterilizable area.

The enclosure (10) is sealed by a glazed wall (22) passed through by interfaces (21) for sterile handling gloves.

It has a transfer system (23) sealed by an alpha part (24), which makes it possible to move a material, for example, a bio-ink cartridge, from one sterile area to another, passing through a non-sterile area, owing to a leaktight and risk-free connection.

Such a system makes it possible to meet the requirements relating to good manufacturing practices (GMP) established by the European Commission within the framework of the development of "quality procedures" and which aim to limit two categories of risks:

the risks of cross-contamination of products (by another product, or an internal and external contaminant);
risks of confusion, in particular, with regard to labeling and identification of components.

They stress hygiene and organizational practices that must be implemented at all levels.

Variant Implementing a "Glove Box" or a Leaktight Hatch

According to a variant not shown, the sterilizable enclosure (10) has a control mechanism for a leaktight device making it possible to perform these tasks in an aseptic or dust-free atmosphere, inside this enclosure, for manual handling of the objects or products. The wall of the enclosure (10), for example, has a flange, the outer periphery of which is fitted with ears intended to cooperate with an impression of the flange of the glove box.

The flange of the enclosure (10) is inserted into the flange of the glove box.

The sterilizable enclosure (10) can also comprise a hatch mounted in a flange for communication with another sterilizable enclosure, for example, for maturation after printing.

Variant Using a Cassette

According to a variant of the present disclosure, the enclosed bioprinting system is based on a sterilizable cassette containing the target (6) and the printhead. It consists of sterile/leaktight interfaces (double leaktight transfer door, beta-bag, optical window, injector, etc.) allowing it to be connected to at least one feed source of objects of biological interest transferable for printing, to one or more activation means, to a mechanical coupling means for the displacement of the target (6) with respect to the head and to the elements necessary for maturation (culture media, $CO_2$, $O_2$, etc.). The cassette can be used for maturation. It can be transported between the printing system and an incubator.

The feed source for transferable objects of biological interest for the printing method can be connected to a cell culture automaton constituted by a dedicated reservoir.

This solution allows biofabrication according to a method that complies with Good Manufacturing Practices (GMP) in a confined enclosure to avoid the risk of biological pollution.

The cassette is coupled to means for characterizing the tissue or organ (online characterization of the tissue during manufacture or after its manufacture) (imaging, Raman spectroscopy, OCT, physicochemical analysis).

The cassette can provide a single window, several windows, windows on both sides (front and back), etc.

The system optionally comprises, for the maturation phase (bioreactor), means for controlling and regulating the following elements:

pH (pH detection range 0-14 and precision 0.01 by $NaOH/CO_2$ regulation),
Temperature (controlled with Peltier, double jacket, cryostat),
dissolved $O_2$ (by gas flow measurement, for example),
hygrometry,
means for removing or changing the culture medium,
stirring and infusion means,
etc.

The cassette optionally comprises an identifier of the tissue to be printed and associated printing parameters (sequence, sources, CAD model, etc.) linked to databases (connected cassette). The identifier can be of the graphic type (for example, bar code or QR code matrix code) or of the digital type, for example, in the form of a numerical sequence recorded in a memory of a radio frequency tag of the RFT type. Such a solution makes it possible to secure the printing process. The cassette is optionally equipped with a network interface card, of the Ethernet port type, to control the manufacturing and data acquisition method, to manage alarms, to save the experiment on local hard drive, to inform the user in real time by SMS, e-mail, etc.

Unit With Glove Box

Figure 10:
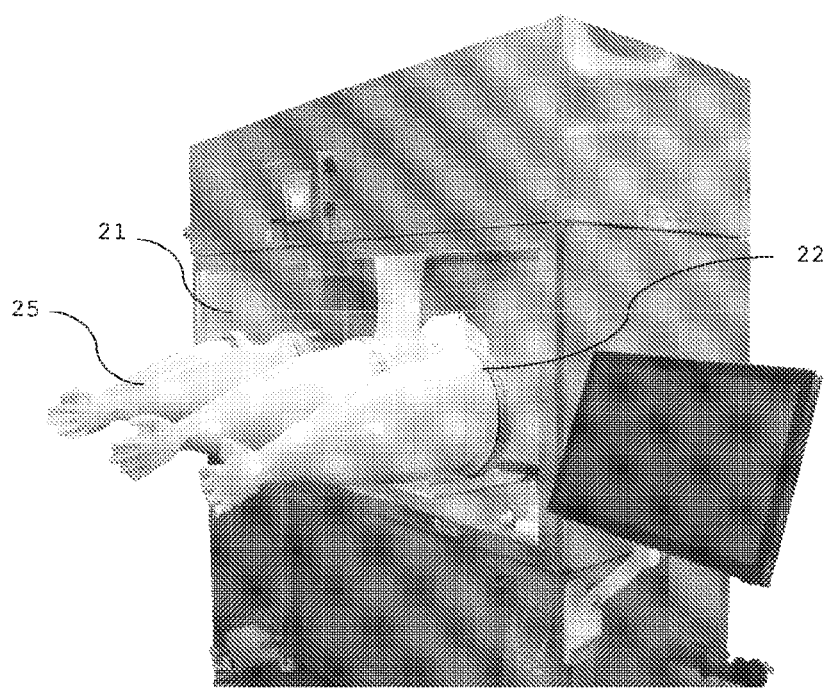
FIG. 10 shows a view of a unit according to the present disclosure with a sterile glove box.
Figure 11:
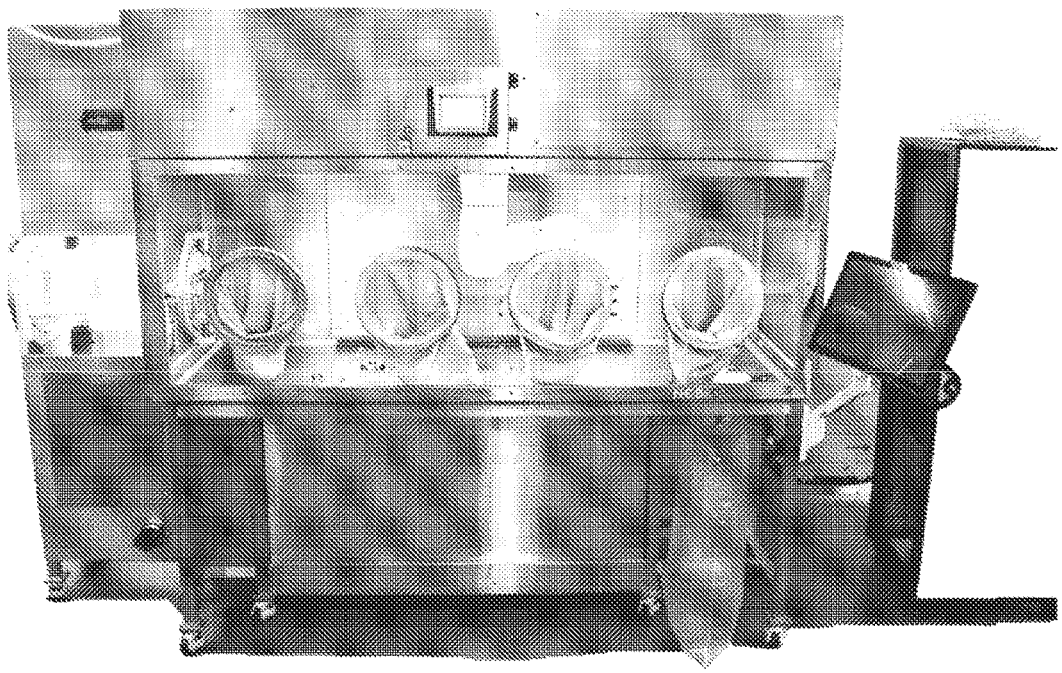
FIG. 11 shows a view of a unit according to the present disclosure with a sterile glove box.
Figure 12:
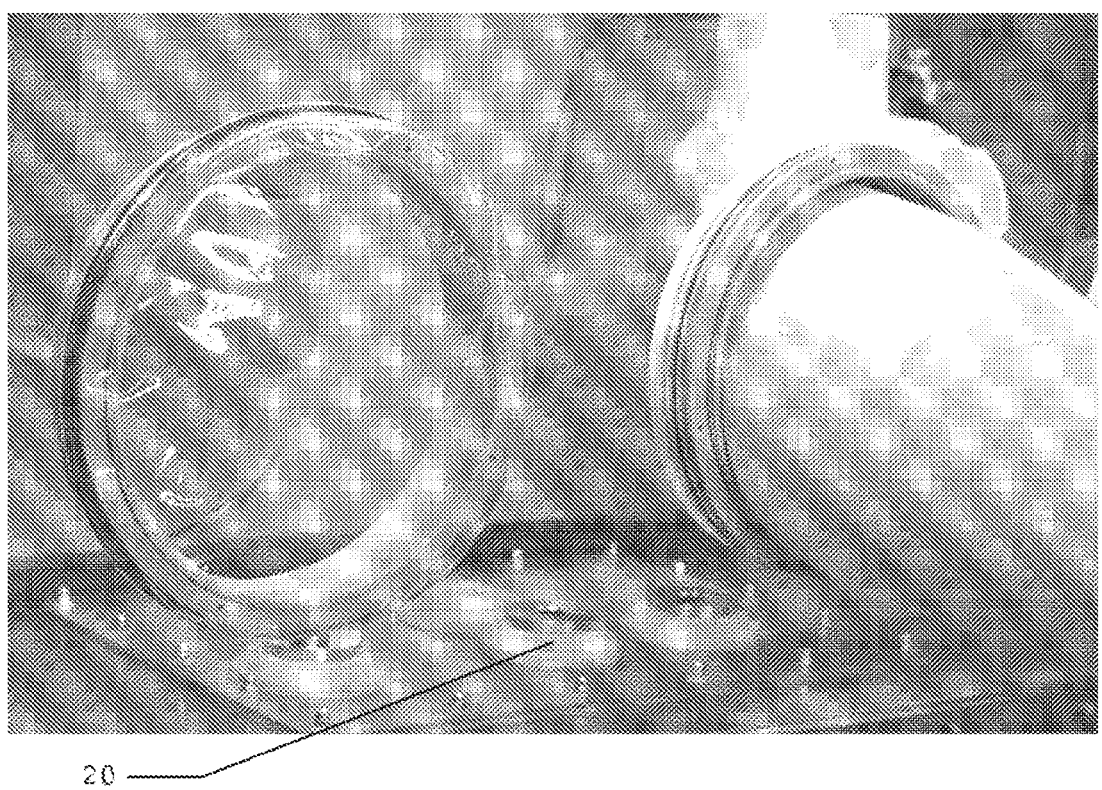
FIG. 12 shows a view of a unit according to the present disclosure with an alpha transfer system with interlocking secured with a beta-type container.

FIGS. 10 and 11 show examples of units with glove boxes (25).

The implementation of the printing methods in the context of a glove box equipped with leaktight hatches (21) can take the following form:

Laser printing: The laser printing module (1) consists of at least one laser head and a target (6). The laser head consists of a transparent flat surface (also called a donor) on which an ink film is deposited. The ink feed source (2) of the head is constituted either by a reservoir, which has been placed in the sterile enclosure owing to the use of an SAS (manual spreading of the ink on the surface of the donor owing to the leaktight glove or owing to the robot associated with a pipettor) or by a reservoir and a pump (working in pressure or in flow) located outside the enclosure (automatic spreading of the ink by fluidic means). The activation means (5) for activating the transfer of the ink to the target (6) consists of a laser located outside the enclosure. The leaktight interaction means (20) is in this case a leaktight optical window transparent to the wavelength of the laser. The means (3) for the relative displacement of the printhead with respect to the target (6) consists of a 6-axis robotic arm.

Microvalve printing: The microvalve printing module (1) consists of a target and one or more valves equipped with a needle that can have different shapes, lengths and opening diameters (6). The ink feed source (2) for the valve consists of a reservoir and a pressurizing pump located outside the enclosure. The activation means (5) for activating the transfer of the ink to the target (6) consists of a shutter of the piezoelectric type or a solenoid. The sealed interaction means (20) can in this case be a connector, a perforable cap (septum) or a leaktight seal. The means (3) for the relative displacement of the printhead with respect to the target (6) consists of a 6-axis robotic arm.

Extrusion printing: The extrusion printing module (1) consists of a target and a final reservoir equipped with a needle, which can have different shapes, lengths and opening diameters (6). The ink feed source (2) for the extruder is constituted by an initial reservoir and a pressurizing pump located outside the enclosure. The activation means (5) for activating the transfer of the biological objects to the target (6) consists of the pressurizing system. The sealed interaction means (20) can in this case be a connector, a perforable cap (septum) or a leaktight seal. The means (3) for the relative displacement of the printhead with respect to the target (6) consists of a 6-axis robotic arm.

With this kind of configuration, tissue manufacturing that meets GMP manufacturing requirements is possible. Thus, clinical batches can be produced safely for the patient. By way of illustration, mention may be made of the example of the manufacture of an autologous or allogeneic skin substitute for regenerative medicine applications. Thus, the different modalities mentioned here make it possible in turn to manufacture:

a dermis made up of alternating layers of biomaterials (collagen type) printed either by microvalve or by extrusion and cell layers (fibroblast type) printed by laser. The precision of the cellular patterns makes it possible to ensure a structure and a function of the dermis close to that of native skin after maturation.

An epidermis made up of a confluent layer of cells (keratinocyte type) printed by laser.

Maturation of this dermis is carried out in an incubator either inside or outside the sterile enclosure depending on the arrangement of the incubator. At the end of this step, the skin has reached maturity and can be implanted in a patient.

Applications for the Fabrication of Biological Tissues

The cassette configuration is particularly suitable for the manufacture of one or more tissues or biological organs, intended, for example, for the manufacture of autologous tissues.

A tissue or an organ can be based on the use of several cassettes for reasons of differentiated maturation, compatibility of the printing module with a single cell type, etc.

Another advantage of the cassette lies in the fact that it can be introduced into the operating room after a final sterilization step and opened as close as possible to the patient.

The substrate could be encapsulated in a module, which is removable from the cassette in order to be placed in a dedicated bioreactor.

The cassette may be wholly or partly disposable.

The cassette can be reused after internal and external sterilization.

The jacket of the cassette can be rigid or flexible ethylene vinyl acetate, PVC, thermoplastics of the PU type, low-density polyethylene, of the transfusion material, silicone, metallic (stainless steel 304L, 316L) or plastic (polycarbonate, for example) type.

Rigid Cassette

FIG. 4 shows an embodiment of the present disclosure in the form of a rigid cassette. It makes it possible to use a main equipment item consisting of the complex and expensive parts, namely the activation means with one or more printheads, for example, laser, a means (3) of relative displacement of the printhead with respect to the target (6) and all of the IT and optical means.

The cassette consists of a sterilizable sealed enclosure (10) configured to allow it to be positioned on this equipment item for a specific operation.

The cassette contains, in the sealed and sterilizable enclosure (10), the specific means, namely:

the printing module (100) consisting of the target (6) (110) on which are deposited the objects of biological interest constituting the tissues to be manufactured, connecting rods (131, 132, 133) ensuring the coupling with the relative displacement means and passing through the enclosure (10) by leaktight seals (134, 135, 136). These connecting rods (131, 132, 133) are intended to transmit the movements of the relative displacement members of the target (6) with respect to the source along the three axes X, Y, Z, the printing module (1), which is constituted by a fluid flow support carrying the transferable objects of biological interest with a feed duct (141) and an outlet duct (142), connected to reservoirs (143, 144) outside the enclosure (10).

The activation means (5) is located outside the sterilizable sealed enclosure (10) and interacts with the printing module (1) via a window (140).

The coupling between the cassette and the fixed equipment item is ensured by magnets surrounding the window (140).

This cassette makes it possible to prepare a tissue by positioning it on the main equipment item, then to ensure the maturation of the bioprinted tissues in another site, for example, in a maturation enclosure.

Flexible Cassette

FIG. 5 shows an embodiment of the present disclosure in the form of a flexible cassette. It differs from the rigid cassette in that the sterilizable enclosure has flexible walls (200) connecting a rigid upper face (210) and a rigid lower face (220), presenting the window (140).

The upper face has two prongs (211, 212) located inside the sterilizable enclosure, in order to receive the target (6) on which the biological elements are deposited transferred from the bio-ink consisting of transferable objects of biological interest (148).

Alternative Embodiments

Regardless of the bioprinting technology used, a bioprinter is traditionally made up of several essential members:
- one or more printheads comprising a bio-ink transfer area made up of objects of biological interest,
- one or more feed sources (2) for feeding the printhead (1) with bio-ink consisting of objects of biological interest,
- a target (6),
- a mechatronic assembly (3) ensuring the relative displacement of the transfer area with respect to the target (6),
- an activation means (5),
- optionally, a maturation area (4).

According to a first variant, the biological ink is stored in a reservoir and passes through nozzles or capillary tubes to form droplets, which are transferred to a target (6).

This first so-called nozzle printing variant encompasses bioextrusion, inkjet printing or microvalve printing. In order to be able, in particular, to achieve a higher level of resolution and increase the viability of the printed cells, a method for printing biological elements without a nozzle has been developed. This printing method, called laser bioprinting, is also known under the name of "Laser-Assisted Bioprinting" (LAB).

Regarding bioextrusion, various means of activating the printing have been implemented: a worm drive, a piston or even a pneumatic system. It makes it possible to work with a high cell density on the order of 100 million cells per milliliter and a resolution on the order of a millimeter. Bioextrusion consists in mechanically pushing biological elements placed in a micro-syringe through a nozzle or a needle having a diameter of a few hundred micrometers. The advantage of this technology lies in its low cost and its simplicity of implementation. However, it suffers from limitations associated with a coarse resolution and a non-negligible cell mortality linked to the shear imposed on the cells during their passage through the nozzle.

Regarding inkjet bioprinting, it consists in projecting micro-droplets of a liquid containing cells or a biomaterial onto a substrate. The projection is caused by a thermal or piezoelectric method. Thermal inkjet printing works by the transient activation of an electrical resistance (with a strong thermal effect), which produces a vapor bubble that propels a droplet through an orifice 30 to 200 μm in diameter.

Piezoelectric inkjet printers use an electrical pulse that generates a change in shape of a piezoelectric crystal, which contracts the ink reservoir. The relaxation of the crystal causes the ejection of the drop. This technique has the advantage of being fast, whether in terms of preparation time or printing speed. However, the main drawbacks of this technology concern the cell concentration not to be exceeded during printing (less than 5 million cells/mL) to prevent clogging of the printheads, as well as the cell death resulting from the shear stress on the cells at the time of passage through the orifice. Inkjet printing, whether by piezoelectric or thermal technology, provides a better resolution of around 10 μm.

Concerning printing by microvalve, the activation means of the printing is the pressurization of the liquid by compressed air. The liquid to be printed is released by actuating a solenoid valve. Micro-valve bioprinting is similar to inkjet technologies, but differs in that the inkjet is formed by pressurizing the ink and then quickly opening a solenoid valve. Having the same constraints as inkjet bioprinting, this technology has the advantage of being able to print more viscous solutions than inkjet systems. Typically, the pressure is from a few hundred mbar to a few bars and makes it possible to obtain a lower cell density on the order of a few million cells per milliliter and a resolution on the order of a few tens of μm.

Laser bioprinting can print inks with a high cell density on the order of 100 million cells per milliliter with a resolution of 10 μm. A device for printing biological elements by laser, which is based on the technique called "Laser-Induced Forward Transfer" (LIFT) comprises a pulsed laser source emitting a laser beam, a system for focusing and orienting the laser beam, a donor medium, which comprises at least one biological ink and a recipient substrate positioned so as to receive droplets emitted from the donor medium. According to this printing technique, the laser beam is pulsed and a droplet is generated upon each pulse. The biological ink comprises a matrix, for example, an aqueous medium, in which elements are present, for example, cells, to be deposited on the recipient substrate. The donor medium comprises a slide, which is transparent to the wavelength of the laser beam and which can be coated with an absorbent layer (metallic, polymer, etc.) or not ("sacrificial layer free LIFT") depending on the configurations on which the biological ink is affixed in the form of a film.

Other optical/laser methods can be implemented as a replacement for or in addition to laser bioprinting (imaging of the donor surface/point-and-shoot system/photopolymerization, texturing, cavitation, cutting, etc.) combined with laser scanning using galvanometric mirrors to produce patterns on the recipient substrate.

Whatever technology is used, the manufacture of a biological tissue by bioprinting can be broken down into five stages:
- preprocessing for Computer-Aided Design (CAD) of a digital model that will define the architecture of the biological tissue, i.e., the position in space (x, y, z) of all the constituents of the tissue,
- programming of the printing parameters of the bio-inks (containing cells and/or biomaterials), which leads to defining the physical parameters of the printer and the trajectory of the printheads,
- preparing and formulating the bio-inks made up of transferable objects of biological interest,
- automated, layer-by-layer printing of bio-inks using bioprinters using various technologies, carrying out maturation of the printed tissue, which takes place in a bioreactor to allow the cells to self-organize until the specific biological functions, which are sought to emerge.

Upstream of this sequence, tomographic reconstructions can be carried out, for example, using microscopic, histological or medical imaging; downstream, the bioprinted biological tissues are conditioned before being sent to the user.

The last three steps of the above manufacturing sequence, as well as the packaging step, must be carried out in a perfectly sterile environment that is free of any particles likely to contaminate the bio-printed tissue, which could alter its growth during maturation and its functionality, and/or infect the patient after tissue implantation.

For this reason, these steps are performed in an enclosure providing a controlled sterile atmosphere and an environment conducive to tissue development.

Laser Printing

The printing assembly (1) consists of one or more laser heads and a target (6).

The laser head(s) consist of a transparent flat surface on which an ink film is deposited either manually by means of a glove box, or by the robot, or by fluidic means linked to the feed source (2).

The feed source (2) for the head is constituted by a reservoir and a pressurizing or flow pump.

The activation means (5) for activating the transfer of the biological objects to the target (6) consists of a laser located outside the enclosure.

The leaktight interaction means (20) is in this case a leaktight optical window transparent to the wavelength of the laser.

The means (3) for relative displacement of the printhead with respect to the target (6) consists of a robotic arm or a mechatronic actuator.

The sterilizable sealed enclosure corresponds to any one of the configurations described above.

Valve Printing

The printing assembly (1) consists of one or more valves and a target (6).

The feed source (2) for the valve consists of a reservoir and a pressurizing pump.

The activation means (5) for activating the transfer of the biological objects to the target (6) consists of a shutter, of the piezoelectric type or a solenoid.

The leaktight interaction means (20) is in this case a perforable cap or a leaktight seal.

The means (3) for relative displacement of the printhead with respect to the target (6) consists of a robotic arm or a mechatronic actuator.

The sterilizable sealed enclosure corresponds to any one of the configurations described above.

Extrusion Printing

The printing assembly (1) consists of one or more extrusion nozzles and a target (6).

The feed source (2) for the nozzle consists of a reservoir and a pressurizing pump.

The activation means (5) for activating the transfer of the biological objects to the target (6) is a control for feeding the nozzle, for example, a mechanical control by a worm drive, or a piston, or a direct pneumatic control.

The leaktight interaction means (20) is in this case a perforable cap or a leaktight seal.

The means (3) for relative displacement of the printhead with respect to the target (6) consists of a robotic arm or a mechatronic actuator.

The sterilizable sealed enclosure corresponds to any one of the configurations described above.

Inkjet Printing

The printing assembly (1) consists of one or more inkjet printheads, and a target (6).

The feed source (2) of the inkjet printhead consists of a reservoir and a feed pump.

The activation means (5) for activating the transfer of the biological objects to the target (6) is a piezoelectric, acoustic, thermal, laser, etc., control.

The leaktight interaction means (20) is in this case a perforable cap or a leaktight seal.

The means (3) for relative displacement of the printhead with respect to the target (6) consists of a robotic arm or a mechatronic actuator.

The sterilizable sealed enclosure corresponds to any one of the configurations described above.

Acoustic Wave Printing

The printing assembly (1) consists of one or more acoustic printheads and a target (6).

The feed source (2) of the acoustic printhead consists of a reservoir and a feed pump.

The activation means (5) for activating the transfer of the biological objects to the target (6) is a transducer, a laser, etc.

The means (3) for relative displacement of the printhead with respect to the target (6) consists of a robotic arm or a mechatronic actuator.

The sterilizable sealed enclosure corresponds to any one of the configurations described above.

Of course, these variant embodiments are not limiting, the present disclosure extending to any technique for depositing a biological element toward a target (6) in a controlled manner for the manufacture of a biological tissue.

The invention claimed is:

1. A bioprinting system for producing biological tissue, comprising:
   a) a printing module containing at least one printhead for printing transferable objects of biological interest and at least one target in a controlled manner for producing a biological tissue;
   b) a feed source for the printhead for printing objects of biological interest;
   c) an activation device configured to transfer the objects of biological interest to the target;
   d) a displacement device configured to cause relative displacement of the printhead with respect to the target; and
   e) a sterilizable sealed enclosure defining a jacket of the printing module, the sterilizable sealed enclosure comprising a movement means, the movement means comprising a magnetic target support interacting with stator coils outside the sterilizable sealed enclosure;
   wherein
      the printing module is located within the sterilizable sealed enclosure;
      the activation device is located outside the sterilizable sealed enclosure and physically separable from the printhead, and mechanically, electrically, acoustically or optically coupled with the printhead, the activation device configured to control the physical transfer of the object of biological interest present in the printhead to the target; and
      the sterilizable sealed enclosure has a leaktight interaction zone with the activation device.

2. The system of claim 1, wherein the sterilizable sealed enclosure further comprises at least one feed source for objects of biological interest.

3. The system of claim 1, wherein the activation device comprises a laser source associated with a beam shaping optic, beam deflection means and a focusing optic, an interface being constituted by a transparent window.

4. The system of claim 1, wherein the activation device comprises a light source capable of interacting with the printhead through a transparent window.

5. The system of claim 1, wherein the activation device comprises a syringe coupled with the printhead.

6. The system of claim 1, wherein the target comprises a volume containing a polymer resin and the printhead comprises injection needles for transferring objects of biological interest.

7. The system of claim 1, further comprising a bioreactor for maturing a fully or partially printed target, the bioreactor being positioned in the sterilizable sealed enclosure.

8. The system of claim 1, further comprising a bioreactor for maturing a fully or partially printed target, the bioreactor being connected by a leaktight means to the sterilizable sealed enclosure.

9. The system of claim 1, further comprising means for physicochemical characterization of evolution of the target during or after printing.

10. A bioprinting system equipped with a bioreactor for maturing a fully or partially printed target, the bioreactor positioned within or connected by a leaktight means to a sterilizable sealed enclosure containing a printing module including at least one printhead for printing transferable objects of biological interest and at least one target in a controlled manner for producing a biological tissue, the sterilizable sealed enclosure defining a jacket of the printing module, the sterilizable sealed enclosure comprising a movement means, the movement means comprising a magnetic target support interacting with stator coils outside the sterilizable sealed enclosure, wherein the bioreactor comprises a feed in a controlled atmosphere.

11. The bioprinting system of claim 10, wherein the bioreactor comprises means for replacing a culture medium contained in the sterilizable sealed enclosure.

12. The bioprinting system of claim 10, wherein the bioreactor comprises means for regulating physicochemical conditions within the sterilizable sealed enclosure.

* * * * *